US008642525B2

(12) United States Patent
Herrwerth et al.

(10) Patent No.: US 8,642,525 B2
(45) Date of Patent: Feb. 4, 2014

(54) FORMULATIONS CONTAINING SORBITAN CARBOXYLIC ACID ESTER

(75) Inventors: Sascha Herrwerth, Essen (DE); Joerg Peggau, Essen (DE); Burghard Gruening, Essen (DE); Uta Kortemeier, Essen (DE); Oliver Springer, Wesel (DE)

(73) Assignee: Evonik Goldschmidt GmbH, Essen (DE)

( * ) Notice: Subject to any disclaimer, the term of this patent is extended or adjusted under 35 U.S.C. 154(b) by 0 days.

(21) Appl. No.: 13/258,802

(22) PCT Filed: Feb. 23, 2010

(86) PCT No.: PCT/EP2010/052252
§ 371 (c)(1),
(2), (4) Date: Sep. 22, 2011

(87) PCT Pub. No.: WO2010/108738
PCT Pub. Date: Sep. 30, 2010

(65) Prior Publication Data
US 2012/0015893 A1    Jan. 19, 2012

(30) Foreign Application Priority Data
Mar. 23, 2009    (DE) .......................... 10 2009 001 748

(51) Int. Cl.
*A61K 8/00*    (2006.01)
(52) U.S. Cl.
USPC ........... 510/119; 510/121; 510/123; 510/130; 510/505
(58) Field of Classification Search
None
See application file for complete search history.

(56) References Cited

U.S. PATENT DOCUMENTS

| 6,544,350 | B2 | 4/2003 | Muller et al. |
| 6,706,502 | B2 | 3/2004 | Gruning et al. |
| 7,186,675 | B2 | 3/2007 | Meine et al. |
| 7,851,511 | B2 | 12/2010 | Allef et al. |
| 2003/0109410 | A1 | 6/2003 | Hahnel et al. |
| 2010/0068160 | A1 | 3/2010 | Springer et al. |

FOREIGN PATENT DOCUMENTS

| AU | 654954 | 12/1994 |
| DE | 10 2004 036 067 A1 | 2/2006 |
| EP | 1 762 216 A1 | 3/2007 |
| EP | 1 813 251 A2 | 8/2007 |
| JP | 51-56809 | 5/1976 |
| JP | 2-67247 | 3/1990 |
| JP | 2000-239697 | 9/2000 |
| JP | 2003-238396 | 8/2003 |
| JP | 2008-169123 | 7/2008 |

OTHER PUBLICATIONS

English Abstract of European Patent Publication No. EP 1619237 A1, dated Jan. 25, 2006.
U.S. Appl. No. 10/126,186, filed Apr. 18, 2002.
International Search Report dated Aug. 8, 2011 issued in PCT/EP2010/052252.

*Primary Examiner* — Necholus Ogden, Jr.
(74) *Attorney, Agent, or Firm* — Scully, Scott, Murphy & Presser, P.C.

(57) ABSTRACT

The invention relates to formulations for the washing and care of human or animal body parts, said formulations containing sorbitan carboxylic acid esters and characterized in that the carboxylic acid part of the sorbitain carboxylic acid ester is derived from a carboxylic acid containing between 6 and 10 carbon atoms and the sorbitan carboxylic acid esters have a hydroxyl count (OH count) of higher than 350. The invention also relates to the use of sorbitan carboxylic acid ester in washing or care formulations.

10 Claims, No Drawings

FORMULATIONS CONTAINING SORBITAN CARBOXYLIC ACID ESTER

FIELD OF THE INVENTION

The invention relates to formulations for the cleansing and care of human or animal body parts containing sorbitan carboxylic acid esters, characterized in that the carboxylic acid component of the sorbitan carboxylic acid ester is derived from a carboxylic acid containing 6 to 10 carbon atoms and the sorbitan carboxylic acid esters have a hydroxyl number (OH number) of greater than 350, and the use of the sorbitan carboxylic acid esters in cleansing or care formulations.

PRIOR ART

Modern cosmetic cleansing products for skin and hair, such as, for example, shower baths and hair shampoos, consist essentially of
  water as the most important solvent,
  surfactants,
  viscosity regulators for thickening the formulation,
  solubilizers for water-insoluble substances,
  perfume oils,
  preservatives and
  active ingredients for the care of skin and hair, such as, for example, moisturizers.

Typical surfactants in body cleansing agents are of anionic, amphoteric and zwitterionic structure. The anionic surfactants in particular include the salts of various cations (sodium, ammonium or other) of lauryl sulfate, lauryl ether sulfate, myristyl ether sulfate, cocoyl glutamates, lauryl glucose carboxylates etc. Cocamidopropylbetaine or cocoamidopropylsultaine are employed, inter alfa, as zwitterionic surfactants. Amphoteric surfactants are, in particular, amphoacetates such as sodium cocoamphoacetate or disodium cocoamphodiacetate.

Typical thickeners employed according to the present state of the art are NaCl, low molecular weight nonionic surfactants, such as coconut fatty acid monoethanolamide/diethanolamide and laureth-3, or polymers, high molecular weight, associative, highly ethoxylated fat derivatives, such as polyethylene glycol (9000)-hydrogenated glyceryl palmitate.

In terms of the present invention, a solubilizer is designated as being a substance that is able to bring water-insoluble compounds into solution in as clear a form as possible in aqueous systems. According to generally accepted belief, in this process aggregates such as micelles are formed, into the structures of which the hydrophobic substances are integrated. The formation of a "microemulsion", that is a thermodynamically stable mixture of water (aqueous solution), an oil (substance not miscible with water) and a solubilizer is optimal. Typical solubilizers are ethoxylated fat derivatives.

Perfume oils are commonly added to the formulations for improving the olfactory properties. Acceptance by the user plays the most important role here. In addition, it is possibly advantageous to mask the intrinsic odors of raw materials used with perfume oils.

Preservatives are employed for microbiological stabilization. In the case of contamination, these ingredients are intended to prevent microbial growth and optionally also kill microorganisms. Preservatives are described in detail and regulated in official regulations (e.g. EU cosmetics directive).

Typical care additives are ethoxylated glycerol fatty acid esters, such as PEG-7 glyceryl cocoate, or cationic polymers, such as polyquaternium-7. These are also designated as moisturizers. During skin cleansing, in addition to the lipophilic dirt the skin's own lipids are also washed off by the surfactants used. This effect is often perceived as unpleasant; the skin feels rough and brittle. The skin is also described as "dry", where here, however, the absence of lipids is meant.

"Moisturizing agents" are added to body cleansing agents in order that the described degreasing process is decreased. As a result, on the one hand the effect produced by the washed off lipid can be compensated by the moisturizing agent, but on the other hand the degreasing action of the formulation can be decreased per se by the use of the moisturizer.

In formulation technology terms, it is difficult to employ emollients (cosmetic oils), such as isopropyl myristate, for this purpose, because these oils have to be laboriously solubilized. More customary moisturizers are therefore more hydrophilic products, such as polyethylene glycol (7) glyceryl monococoate (TEGOSOFT GC®), which are already solubilized by the excess of the cleansing surfactants. The analysis of a product database, which records worldwide product innovations in consumer markets ("Global New Products Database": Mintel), showed that 29% of all skin cleansing formulations in the European market in the period under investigation (9/05-9/06) contained polyethylene glycol (7) glycerylmonococoate.

It is assumed that the moisturizing process takes place on the rinsing off of the formulation after actual washing. In the cleansing process with water, the solution present is diluted until the critical micelle concentration is fallen short of and the lipophilic components solubilized in the surfactant aggregates become insoluble. With the release of the micelle components (the lipophilic moisturizers, the surfactants and solubilizers), the moisturizing agents again become insoluble. These lipophilic substances (both the skin's own lipids and emollients/cosmetic oils) precipitate and are absorbed into the skin.

The requirements of the finished formulation thus include, in addition to the cleansing action, a creamy foam, good foaming behavior, a good foam volume, protection against the drying out of the skin and a good care capacity. The basic requirements of the individual constituents include mildness, in particular good skin compatibility and workability. It is advantageous if as many as possible of the requirements of a cosmetic formulation are able to be fulfilled by as few toxicologically harmless and universally employable constituents as possible.

In addition, there is an increasing need for polyether-free formulations, which contain as few components as possible and which are produced starting from petrochemical, non-renewable raw materials. Therefore an important aim of cosmetic research consists in dispensing with polyether-containing ingredients.

However, polyether-free products according to the prior art do not exhibit the desired property profiles.

Polyether-free formulations exhibit, for example, markedly reduced foaming properties, which is regarded as a marked disadvantage. Furthermore, polyether-free surfactant formulations are markedly more difficult to thicken, since NaCl does not have any thickening properties in such systems. The formulator is therefore forced to resort to the class of associative, highly ethoxylated fat derivatives and relinquishes here the aim of the polyether-free formulations.

It is consequently a matter of abandoning traditional routes and of developing novel polyether-free formulations that replace the conventional polyether-containing formulations, and fulfil the modern requirements of the consumers. For this purpose, novel polyether-free active ingredients having very good application properties are needed.

Sorbitol is the reduced polyol form of glucose, is counted amongst the sugar alcohols and is also known under the name glucitol.

Sorbitol can self-condense with elimination of water, so-called sorbitan being formed here. Sorbitan is in general understood as meaning a product mixture of the self-condensation products of sorbitol; these are essentially five- and six-membered, mono- and bicyclic, hydroxyl-functional ethers of polyol character, as shown exemplarily by the following formulae:

1,4-Sorbitan  1,5-Sorbitan

Isosorbitol

In this mixture, further condensation products and also sorbitol are in general contained to a minor extent.

Sorbitan esters are the esters of sorbitan and thus the esterification products of this above-described polyol mixture with organic acids, the polyol mixture as a rule being esterified with 1 to 3 mol of acid per mol of polyol mixture.

A summary presentation of sorbitan esters is found, for example, in Treon, Soap Perfumery Cosmetics, January 1965, p. 47.

Sorbitan esters are long-known as good and mild emulsifiers, but up to now only longer-chain fatty acid derivatives of monolaurate to tristearate have had industrial importance. Traditional sorbitan esters are at first not water-soluble. They are therefore hydrophilized by ethoxylation if required. For emulsifiability, the desired HLB is adjusted by mixing the hydrophilic and hydrophobic sorbitan esters and thus making possible solubility in various systems.

DE 10 2004 036 067 describes the use of sorbitan esters as cleansing enhancers in aqueous cleansing agent concentrates based on nonionic, anionic or amphoteric surfactants and optionally with co-use of customary auxiliaries and additives for the cleaning of profiled tiles and flagstones.

EP 1813251 describes, inter alia, the use of sorbitan partial esters for the production of polyether-free, cold-manufacturable long-term-stable, low-viscosity and fine-celled oil-in-water emulsions for wet wipes.

U.S. Pat. No. 7,135,168 describes the use of sorbitan esters and ethoxylated sorbitan esters in hair-dyeing compositions.

EP0843713 describes mild hair shampoos containing long-chain fatty acid N-alkylglucamides and sugar surfactants. Inter alia, possible sugar surfactants that are intended to improve the use properties of fatty acid N-alkylglucamides are also sorbitan esters, preferably sorbitan esters of $C_{12}$- to $C_{18}$-carboxylic acids.

Fatty acid N-alkylglucamides are mild polyether-free surfactants that, however, have not found widespread use owing to their involved preparation.

EP1394225 describes water-in-oil thickener dispersions, in which the thickening effect is based on polyelectrolytes, and sorbitan esters of $C_{10}$- to $C_N$-carboxylic acids are employed as the disperser component.

None of the specifications mentioned thus discloses formulations containing sorbitan esters for the cleansing and care of human or animal body parts and the use of sorbitan esters as a viscosity regulator, care agent, foam booster or solubilizer.

It is the object of the present invention to make available formulations that manage with small amounts of conventional thickeners or viscosity regulators and at the same time have a good care performance.

DESCRIPTION OF THE INVENTION

Surprisingly, it has been found that the formulations for the cleansing and care of human or animal body parts described below and the use according to the invention of reaction products of sorbitol achieve this object.

The present invention therefore relates to formulations for the cleansing and care of human or animal body parts containing process products of esterification reactions of sorbitol.

The invention further relates to the use of process products of esterification reactions of sorbitol as a viscosity regulator, care ingredient, foam booster or solubilizer.

An advantage of the invention is the good availability of the components employed and their good toxicological properties, particularly relevant for cosmetic and pharmaceutical applications.

A further advantage is that on account of the high application performance further viscosity regulators and optionally also further moisturizers, foam boosters or solubilizers in the formulation chosen in each case can be dispensed with.

An even further advantage is that the use according to the invention is also possible in polyether-free surfactant formulations as a viscosity regulator, care active ingredient, foam booster or solubilizer.

As established above, many conventional thickeners such as NaCl fail in polyether-free formulations and the high molecular weight, associative thickeners cannot be employed in polyether-free formulations because of their polyether groups.

Furthermore, the foam properties of PEG-free and polyether-free systems are not adequate.

All percentages stated, if not stated otherwise, are percentages by weight.

The present invention thus relates to formulations for the cleansing and care of human or animal body parts containing sorbitan carboxylic acid esters, characterized in that the carboxylic acid component of the sorbitan carboxylic acid ester is derived from a carboxylic acid containing 6 to 10, preferably 8, carbon atoms and the sorbitan carboxylic acid esters have a hydroxyl number (OH number) of greater than 350, preferably of greater than 400, in particular of greater than 450.

Suitable determination methods for the determination of the hydroxyl number are in particular those according to DGF C-V 17 a (53), Ph. Eur. 2.5.3 Method A and DIN 53240.

It is preferred that the formulation according to the invention contains from 0.01% by weight to 10% by weight, preferably 0.05% by weight to 5% by weight, particularly preferably 0.1% by weight to 3% by weight of sorbitan carboxylic acid ester based on the total formulation.

Preferably, the formulations according to the invention are aqueous formulations; these are characterized in terms of the present invention by a water content of at least 50% by weight, preferably at least 75% by weight, particularly preferably at least 80% by weight, based on the total formulation.

It is preferred that formulations according to the invention are surfactant formulations, Since the sorbitan carboxylic acid esters contained in the formulations according to the invention already have surfactant properties as, for example, a sorbitan caprylate-containing composition, in connection with the present invention the term "surfactant formulation" is to be understood as meaning a formulation that, in addition to the sorbitan carboxylic acid ester, contains at least one further surfactant. Further surfactants contained can be, for example, nonionic, anionic or amphoteric surfactants. Typical examples of mild, i.e. particularly skin-compatible surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, ether carboxylic acids, alkyl oligoglucosides, fatty acid glucamides, alkylamidobetaines and/or protein fatty acid condensates, the latter, for example, based on wheat proteins.

Amphoteric surfactants are, for example, betaines, amphoacetates or amphopropionates to be employed, for instance substances such as the N-alkyl-N,N-dimethyl-ammonium glycinates, for example coconut alkyldimethyl-ammonium glycinate, N-acylaminopropyl-N,N-dimethylammonium glycinates, for example coconut acylaminopropyldimethyl-ammonium glycinate, and 2-alkyl-3-carboxylmethyl-3-hydroxy-ethylimidazolines in each case having 8 to 18 C atoms in the alkyl or acyl group, and coconut acylaminoethylhydroxy-ethylcarboxymethyl glycinate.

Ampholytic surfactants are, for example, those surface-active compounds that apart from a C8/18-alkyl or -acyl group in the molecule contain at least one free amino group and at least one —COOH or —$SO_3H$ group and are capable of the formation of internal salts. Examples of suitable ampholytic surfactants are N-alkylglycines, N-alkyl-propionic acids, N-alkylaminobutyric acids, N-alkylimino-dipropionic acids, N-hydroxyethyl-N-alkylamidopropyl-glycines, N-alkyltaurines, N-alkylsarcosines, 2-alkylamino-propionic acids and alkylaminoacetic acids in each case having approximately 8 to 18 C atoms in the alkyl group. Further examples of ampholytic surfactants are N-coconut alkylaminopropionate, coconut acylaminoethylaminopropionate and C12/18-acylsarcosine.

Surfactant formulations according to the invention contain, as a further surfactant, in particular fatty alcohol sulfates, fatty alcohol polyethersulfates, mono- and/or dialkylsulfosuccinates, amphoacetates, amphopropionates, betaines, cocamidopropylbetaines, alkyl oligoglucosides or fatty acid glutamates.

Surfactant formulations according to the invention preferably contain as a further surfactant those surfactants which are essentially free of polyethers and polyether-containing compounds.

Particularly preferably, surfactant formulations according to the invention contain as further surfactants the polyether-free surfactants mono- and/or dialkyl sulfo-succinates, amphoacetates, amphopropionates, betaines, in particular cocamidopropylbetaine, alkyl oligoglucosides or fatty acid glutamates.

Preferred surfactant formulations according to the invention contain at least 20 by weight, preferably at least 4% by weight and particularly preferably at least 60 by weight of at least one further surfactant based on the total formulation.

Particularly preferred formulations according to the invention are aqueous surfactant formulations containing at least 0.01% by weight of sorbitan carboxylic acid ester, at least 5% by weight of at least one further surfactant and at least 75% by weight of water based on the total formulation, in particular those containing at least 0.3% by weight of sorbitan carboxylic acid ester, at least 6% by weight of at least one further surfactant and at least 80% by weight of water based on the total formulation.

Preferably, formulations according to the invention are liquid, cosmetic, dermatological or pharmaceutical body cleansing compositions, in particular shower baths and gels, bath formulations, liquid soaps and shampoos.

For formulations preferred according to the invention, it thus holds that the human or animal body parts are preferably hair or skin.

Since the object of the invention, contrary to current expectations, cf. above, is also achieved in polyether-free formulations, preferred formulations according to the invention are in particular those which are characterized in that the formulation is essentially free of polyethers and polyether-containing compounds.

Likewise, preferred formulations according to the invention are those which are characterized in that the formulation is free of fatty acid N-alkylglucamides.

The term "essentially free of polyethers and polyether-containing compounds" in connection with the present invention describes that contained compounds contain alkoxy groups, oligoalkoxy groups or polyalkoxy groups such as ethylene oxide or propylene oxide only in traces, preferably none. The concentration of polyether-containing compounds should be less than 0.1% by weight, particularly preferably less than 0.01% by weight based on the total formulation, preferably below the detection limit of current analysis methods such as, for example, NMR spectroscopy, GPC or Maldi.

The same applies for the term "free of fatty acid N-alkylglucamides".

On account of the good availability and the simple handling, formulations according to the invention preferably contain sorbitan carboxylic acid ester in which the carboxylic acid content is derived from ethylhexanoic acid or caprylic acid, preferably caprylic acid.

It is obvious that it makes sense in connection with the invention that formulations according to the invention preferably sorbitan carboxylic acid ester in which the carboxylic acid content is derived from technical caprylic acid, in particular from technical caprylic acid from native raw materials, such as is obtained, for example, from palm oil or coconut oil.

This technical caprylic acid can comprise carboxylic acids having a chain length of 6 to 10 carbon atoms, the essential component being formed by carboxylic acids having a chain length of 8 carbon atoms: "essential component" is to be understood as meaning at least 50% by weight, preferably 80% by weight, in particular 90% by weight based on the total weight of the technical acid mixture.

Formulations according to the invention particularly preferably contain sorbitan carboxylic acid esters which are characterized in that they have an acid number of less than 20, preferably of less than 15, in particular of less than 10. Suitable determination methods for the determination of the acid number are in particular those according to DGF C-V 2, Ph. Eur. 2.5.1, ISO 3682, ASTM D 974 and DIN EN ISO 2114.

Formulations according to the invention particularly preferably contain sorbitan carboxylic acid esters which are characterized in that they have an iodine number of less than 30, preferably of less than 10, in particular of less than 5.

Suitable determination methods for the determination of the iodine number are in particular those according to DGF C-V 11 a (53), Ph. Eur. 2.5.4 Method A and DIN 53241.

Formulations according to the invention particularly preferably contain sorbitan carboxylic acid esters which are characterized in that they have a viscosity of 100 to 20 000 mPa·s, preferably of 1000 to 15 000 mPa·s, in particular of 2000 to 10 000 mPa·s.

A suitable determination method for the determination of the viscosity is in particular that according to DIN 53015.

Formulations according to the invention particularly preferably contain sorbitan carboxylic acid esters, in which 1 to 3 mol, preferably 1.2 to 2 mol, in particular 1.4 to 1.6 mol, of carboxylic acid per one mole of sorbitol from which the sorbitan carboxylic acid ester is derived are esterified in.

Formulations according to the invention particularly preferably contain sorbitan carboxylic acid esters commercially obtainable (Evonik Industries) under INCI name sorbitan sesquicaprylate.

The preparation of the sorbitan carboxylic acid esters contained in formulations according to the invention can be carried out by condensation and esterification or trans-esterification reactions of sorbitol with carboxylic acids or their esters. In this preparation, depending on specificity of the process, the reactions can be carried out in succession or parallel.

Formulations according to the invention in particular contain sorbitan carboxylic acid esters obtainable by, preferably obtained by a process comprising the process steps A) dehydration of sorbitol, B) reaction of the dehydrated sorbitol with at least one compound selected from the group comprising carboxylic acids containing 6 to 10, preferably 8, carbon atoms, carboxylic acid esters or carboxylic acid ester mixtures, in which the carboxylic acid component contains 6 to 10, preferably 8, carbon atoms, and optionally C) isolation of formed sorbitan esters from process step B).

In process step A), the sorbitol is dehydrated to give various isomers, for instance to give 1,4- and 3,6-sorbitan. The reaction conditions in process step have an influence on the composition of the dehydration product. Formulations according to the invention are distinguished in that sorbitan carboxylic acid esters are preferably contained, in whose preparation process step A) is carried out at a temperature between 100° C. and 180° C., preferably between 120° C. and 160° C., in particular between 130° C. and 150° C.

In addition, formulations according to the invention are distinguished in that sorbitan carboxylic acid esters are preferably contained, in whose preparation process step A) is carried out at a pressure between 0.001 bar and 1.5 bar, preferably between 0.5 bar and 1.25 bar, in particular between 0.8 bar and 1.2 bar.

In a preferred, alternative embodiment of formulations according to the invention, sorbitan carboxylic acid esters are employed, in whose preparation process step A) is carried out at a pressure between 0.001 bar and 0.9 bar, preferably between 0.005 bar and 0.5 bar, in particular between 0.006 bar and 0.01 bar and at a temperature between 80° C. and 140° C., preferably between 90° C. and 130° C., in particular between 95° C. and 120° C.

The use of an acid catalyst, as described for example in EP 0280780, can have an influence on the dehydration product. Formulations according to the invention preferably contain sorbitan carboxylic acid esters, in which process step A) is carried out with an acid catalyst, preferably phosphoric acid.

A quick and if possible quantitative reaction in process step B) is dependent on the various parameters such as pressure, temperature and qualitative ratio of the reaction partners to one another. These parameters likewise influence the sorbitan carboxylic acid esters with respect to statistical distribution, for example of various isomers, produced by, for example, different possibilities of the esterification position in the molecule, which can lead to mixtures of mono-, di- and even triesters.

Formulations according to the invention preferably contain sorbitan carboxylic acid esters which are characterized in that process step B) is carried out at a temperature between 140° C. and 260° C., preferably between 160° C. and 250° C., in particular between 200° C. and 230° C. Analogously, it is preferable that process step B) is carried out at a pressure between 0.001 bar and 1.5 bar, preferably between 0.5 bar and 1.25 bar, in particular between 0.8 bar and 1.2 bar.

In a preferred, alternative embodiment of formulations according to the invention, sorbitan carboxylic acid esters are employed in whose preparation process step B) is carried out at a pressure between 0.001 bar and 0.9 bar, preferably between 0.05 bar and 0.5 bar, in particular between 0.006 bar and 0.01 bar and at a temperature between 80° C. and 250° C., preferably between 120° C. and 220° C., in particular between 150° C. and 200° C.

Just as in process step A), the use of a catalyst in process step B), such as alkali metal hydroxides, alkali metal carbonates or alkali metal salts of phosphoric acid, phosphorous acid or hypophosphorous acid can have an influence on the sorbitan carboxylic acid esters.

Formulations according to the invention preferably contain sorbitan carboxylic acid esters, in whose preparation in process step B) at least one catalyst selected from the group comprising alkali metal salts and alkaline earth metal salts, preferably sodium hydroxide, is employed.

It is obvious that in connection with the invention, it makes sense that technical caprylic acid, in particular technical caprylic acid from native raw materials, such as is obtained from palm oil or coconut oil, is to be employed in process step B) as the carboxylic acid.

With respect to the composition of the technical caprylic acid, see above.

The formulations according to the invention can contain sorbitan carboxylic acid esters, in which in process step B) carboxylic acid esters of any carboxylic acid containing 8 carbon atoms are employed; it is preferable in this connection, however, that the carboxylic acid ester employed is an ester of a carboxylic acid containing 8 carbon atoms with at least one alcohol selected from the group comprising glycerol, methanol and ethanol.

In a manner analogous to above it is preferred that the carboxylic acid ester employed is preferably an ester of ethylhexanoic acid or caprylic acid, the caprylic acid being derived as described above, in particular from technical caprylic acid, in particular from technical caprylic acid from native raw materials.

In particular, carboxylic acid esters from native raw materials, such as glycerol esters of caprylic acid from goat's butter, milk, palm oil and coconut oil or from wine fusel oil can also be employed as carboxylic acid esters in process step B).

It is evident to the person skilled in the art that mixtures of various starting materials can similarly be employed in the different process steps, and mixtures of sorbitan carboxylic acid esters can be contained in the formulations according to the invention.

It is obvious that the properties of the formulations according to the invention can be influenced by the quantitative ratio of carboxylic acid or carboxylic acid ester to sorbitol employed in the process.

Formulations according to the invention are distinguished in that preferably sorbitan carboxylic acid esters are contained, in whose preparation the molar ratio of sorbitol employed in process step A) to reaction partner employed in process step B) is between 1:1 and 1:3, preferably between 1:1.2 and 1:2, in particular between 1:1.4 and 1:1.6.

Since from the process technological point of view it can be advantageous if process step A) and B) are started by parameters easily capable of being influenced from outside, formulations according to the invention preferably contain sorbitan carboxylic acid esters which are characterized in that all substances employed in process step A) and B) are contained at the start of process step A); preferably in this connection process step B) is initiated by a dynamic temperature increase.

In process step C), an isolation of sorbitan ester formed can be carried out.

For the isolation of the sorbitan ester, possible methods are all methods known to the person skilled in the art for the isolation of to molecular weight substances from complex compositions. By way of example, at this point precipitation by means of suitable solvents, extraction by means of suitable solvents, complexation, for example by means of cyclodextrins or cyclodextrin derivatives, crystallization, purification or isolation by means of chromatographic methods or conversion of the sorbitan esters to easily separable derivatives may be mentioned. Formulations according to the invention preferably contain sorbitan carboxylic acid esters that were obtained without process step C).

The care formulations according to the invention can contain, for example, at least one additional component, selected from the group consisting of the
- emollients,
- emulsifiers,
- thickeners/viscosity regulators/stabilizers,
- UV lightscreen filters,
- antioxidants,
- hydrotropes (or polyols),
- solids and fillers,
- film formers,
- pearl luster additives,
- deodorant and antiperspirant active ingredients,
- insect repellents,
- self-tanning agents,
- preservatives,
- conditioners,
- perfumes,
- colorants,
- cosmetic active ingredients,
- care additives,
- superfatting agents,
- solvents.

Substances that can be employed as exemplary representatives of the individual groups are known to the person skilled in the art and can be taken, for example, from German application DE 102008001788.4. This patent application is hereby inserted as a reference and is thus considered as part of the disclosure.

A further subject of the present invention is the use of sorbitan carboxylic acid esters in which the carboxylic acid content is derived from a carboxylic acid containing 6 to 10, preferably 8, carbon atoms and which have a hydroxyl number (OH number) of greater than 350, preferably of greater than 400, in particular of greater than 450, as a viscosity regulator, care active ingredient, foam booster or solubilizer in cleansing or caring formulations.

The cleansing or caring formulations, in which the sorbitan carboxylic acid esters are used according to the invention, are preferably cosmetic, dermatological or pharmaceutical formulations, preferably for the cleansing and care of human or animal body parts, particularly preferably surfactant, in particular aqueous surfactant formulations for the cleansing and care of human or animal body parts, in particular of skin and hair.

Further preferred formulations, in which the sorbitan carboxylic acid esters are used according to the invention, are preferred formulations according to the invention described above.

Preferably, in use according to the invention, sorbitan carboxylic acid esters are used, which in the context of the formulations according to the invention described above are preferably contained in the formulations according to the invention.

In the examples mentioned below, the present invention is described by way of example without it being intended to restrict the invention, whose breadth of application results from the entire description and the claims, to the embodiments mentioned in the examples,

EXAMPLES

All concentrations in the use examples are stated in percentages by weight. Customary formulation processes known to the person skilled in the art were used for the preparation of the formulations.

Example 0

Preparation of Sorbitan Carboxylic Acid Ester 390.45 g of sorbitol syrup, a 70% strength aqueous solution, 2.9 g of phosphoric acid and 5.0 g of sodium hydroxide were weighed into a flask and dehydrated at atmospheric pressure and at 140° C. for 30 min. Subsequently, 334.8 g of caprylic acid were added and esterified at 200° C. and atmospheric pressure. After the reaction time, the product was filtered through a filter press. The product obtained is clear, has a final viscosity of about 6000 mPa·s, a hydroxyl number of 470, an acid number of <10 and an iodine number of <1, determined according to the process described above.

The substance obtained was employed in the following examples and is designated below by Cap01

Example 1

Testing of the Thickening Properties

The thickening action of Cap01 from Example 0 was tested in comparison to customary surfactant thickeners in various surfactant systems.

The viscosities were measured at 25° C. by means of a Brookfield viscometer (Brookfield LVF, spindle 3, 5 rpm).

1a) Surfactant System 1a:

32% by weight of sodium lauryl ether sulfate (Cognis, Texapon® NSO, 28% strength), 8% by weight of cocamidopropylbetaine (Evonik Goldschmidt GmbH, TEGO® betaine F 50, 38% strength) and 0.7% by weight of NaCl were adjusted at 25° C. to a viscosity of 3500 mPas. The thickener concentration needed in each case for this is shown in Table 1-1. It is seen that Cap01 from Example 0 is most effective in comparison to commercially available thickeners, as the lowest use concentration is needed.

TABLE 1-1

Thickening action of Cap01 in comparison to commercially available thickeners.

|  | % by weight | % by weight | % by weight |
|---|---|---|---|
| Texapon NSO ® (Cognis, INCI: Sodium Laureth Sulfate, 28% strength) | 32.0 | 32.0 | 32.0 |
| TEGO ® betaine F 50 (Evonik Goldschmidt GmbH, INCI: Cocamidopropyl Betaine, 38% strength) | 8.0 | 8.0 | 8.0 |
| Cap01 | 1.1 | | |
| REWOMID ® DC 212 S (Evonik Goldschmidt GmbH, INCI: Cocamide DEA)* | | 1.5 | |
| Tegosoft ® PC 31 (Evonik Goldschmidt GmbH, INCI: Polyglyceryl-3 Caprate)* | | | 2.4 |
| NaCl | 0.7 | 0.7 | 0.7 |
| Water, demineralized | | to 100.0 | |
| Viscosity [mPas], | | 3500 | |

*Comparison example not according to the invention

1b) Surfactant System 1b:

32% by weight of sodium lauryl ether sulfate (Cognis, Texapon® NSO, 28% strength) and 9% by weight of sodium cocoamphoacetate (Evonik Goldschmidt GmbH, Rewoteric® AM C, 32% strength) were adjusted to a viscosity at 25° C. of 3500 mPas. The thickener concentration needed in each case for this is shown in Table 1-2. It is seen that Cap01 is most effective in comparison to commercially available thickeners, as the lowest use concentration is needed,

TABLE 1-2

Thickening action of Cap01 in comparison to commercially available thickeners.

|  | % by weight | % by weight | % by weight |
|---|---|---|---|
| Texapon ® NSO (Cognis, INCI: Sodium Laureth Sulfate, 28% strength) | 32.0 | 32.0 | 32.0 |
| Rewoteric ® AM C (Evonik Goldschmidt GmbH, INCI: Sodium Cocoamphoacetate, 32% strength) | 9.0 | 9.0 | 9.0 |
| Cap01 | 1.5 | | |
| REWOMID ® DC 212 S (Evonik Goldschmidt GmbH, INCI: Cocamide DEA)* | | 1.9 | |
| Tegosoft ® PC 31 (Evonik Goldschmidt GmbH, INCI: Polyglyceryl-3 Caprate)* | | | 3.9 |
| Water, demineralized | | to 100.0 | |
| Viscosity [mPas], | | 3500 | |

*Comparison example not according to the invention

1c) Surfactant System 1c:

15% by weight of sodium cocoamphoacetate (Evonik Goldschmidt GmbH, Rewoteric® AM C, 32% strength), 13% by weight of cocamidopropylbetaine (Evonik Goldschmidt GmbH, TEGO® betaine F 50, 38% strength) and 3.8% by weight disodium lauryl sulfosuccinate (Evonik Goldschmidt GmbH, Rewopol® SB F 12 P, 95% strength) was adjusted at 25° C. to a viscosity of 3500 meas. This is a PEG-free surfactant formulation, which is difficult to thicken, In Tab. 1-3, it is shown what use concentration of the commercially available thickener ANTIL® HS 60 (Evonik Goldschmidt GmbH, INCI: Cocamidopropyl Betaine; Glyceryl Laurate) is needed in comparison to the combination Cap01+ANTIL® HS 60 (Evonik Goldschmidt GmbH, INCI: Cocamidopropyl Betaine; Glyceryl Laurate). It is obvious that a synergistic action occurs in the case of the use of the combination Cap01+ANTIL® HS 60 (Evonik Goldschmidt GmbH, INCI: Cocamidopropyl Betaine; Glyceryl Laurate) and a significant reduction in the amount of thickener needed of 4.5% by weight to 1.5% by weight can be achieved. A saving of resources also occurs here, as markedly fewer active thickener ingredients are needed.

TABLE 1-3

Thickening action of Cap01 in a PEG-free formulation in comparison to commercially available thickeners.

|  | % by weight | |
|---|---|---|
| Rewopol ® SB F 12 P (Evonik Goldschmidt GmbH, INCI: Disodium Lauryl Sulfosuccinate, 95% strength) | 3.8 | 3.8 |
| TEGO ® betaine F 50 (Evonik Goldschmidt GmbH, INCI: Cocamidopropyl Betaine, 38% strength) | 13 | 13 |
| Rewoteric ® AM C (Evonik Goldschmidt GmbH, INCI: Sodium Cocoamphoacetate, 32% strength) | 15 | 15 |
| Cap01 | 0 | 0.5 |
| Antil HS 60 | 4.5 | 1 |
| Water, demineralized | to 100.0 | |
| Viscosity [mPas], | 3500 | |

1d) Use of Cal01 as a Thickener in Cleansing Formulation for Hard Surfaces

| % active contents | Gel 1 | Gel 2 |
|---|---|---|
| Texapon ® NSO (Cognis, INCI: Sodium Laureth Sulfate, 28% strength) | 48.6 | 48.6 |
| TEGO ® betaine F 50 (Evonik Goldschmidt GmbH, INCI: Cocamidopropyl Betaine, 38% strength) | 9.0 | |
| Rewoteric ® AM C (Evonik Goldschmidt GmbH, INCI: Sodium Cocoamphoacetate, 32% strength) | | 10.6 |
| NaCl | 0.7 | |
| Cap01 | 1.8 | 1.8 |
| Water | | |
| Appearance | Clear | Clear |
| pH | | |
| Viscosity [mPas] | 23 000 | 5900 |

Example 2

Testing of the Conditioning of Skin (Skincare Performance) and Foam Properties by Means of a Handwashing Test For the assessment of the moisturizing care of skin (skincare performance) and the foam properties of Cap01 in aqueous, surfactant formulations, sensory handwashing tests were carried out in comparison to the market standard polyethylene glycol (7) glycerylmonoacetate.

Polyethylene glycol (7) glycerylmonococoate is widespread in industry as a moisturizing care active ingredient and recognized as a highly active component in aqueous, surfactant formulations.

A group consisting of 10 trained test subjects washed their hands here in a defined manner and assessed foam properties and skin sensation by means of a grading scale of 1 (poor) to 5 (very good). The products employed were in each case tested in a standardized surfactant formulation (Tables 2-1 and 2-3).

2a) Hand Washing Test in a Conventional Polyether-Containing Surfactant Formulation The control formulation 2a1 used is a formulation without addition of an additive.

TABLE 2-1

Test formulations for handwashing test.

|  | Formulation examples | | |
|---|---|---|---|
|  | 2a1* | 2a2 | 2a3* |
| Texapon NSO ® (Cognis, INCI: Sodium Laureth Sulfate, 28% strength) | 32% | 32% | 32% |
| TEGO ® betaine F 50 (Evonik Goldschmidt GmbH INCI: Cocamidopropyl Betaine, 38% strength) | 8% | 8% | 8% |
| NaCl | 2% | 2% | 2% |
| water, demineralized |  | to 100% |  |
| Cap01 |  | 1.0% |  |
| Tegosoft ® GC (Evonik Goldschmidt GmbH, INCI: Polyethylene glycol(7)glycerylmonococoate) |  |  | 1.0% |

*Comparison example not according to the invention

The test results are summarized in Table 2-2.

TABLE 2-2

Results of the handwashing test

|  | Test formulation | | |
|---|---|---|---|
|  | 2a1* | 2a2 | 2a3* |
| Foaming behavior | 3.1 | 3.7 | 3.1 |
| Foam volume | 2.6 | 3.4 | 2.6 |
| Foam creaminess | 2.6 | 3.4 | 2.6 |
| Skin sensation during washing | 3.0 | 4.0 | 3.6 |
| Skin smoothness directly after application | 1.6 | 2.7 | 2.3 |
| Skin softness directly after application | 2.0 | 3.1 | 2.7 |
| Skin smoothness after 3 min. | 3.0 | 3.6 | 3.4 |
| Skin softness after 3 min. | 3.0 | 3.5 | 3.3 |

*Comparison example not according to the invention

The results of the handwashing test are shown in Table 2-2. By means of the measured results it is evident that the formulation 2a2 according to the invention using Cap01 brings about a better skin smoothness and skin softness 3 minutes after application and a superior skin sensation during washing in comparison to the comparison formulations 2a1 and 2a3 according to the prior art. The skin smoothness and skin softness directly after application is also superior in the case of the formulations 2a2 according to the invention to the measured values in the case of the comparison formulations 2a1 and 2a3. In addition, it is evident by means of the measured values that the formulation 2a2 according to the invention containing Cap01 brings about an improvement of the foaming properties.

2b) Hand Washing Test in a Polyether-Free Surfactant Formulation:

A formulation without addition of an additive is used as the control formulation 2a4.

TABLE 2-3

Test formulations for handwashing test.

|  | Formulation examples | |
|---|---|---|
|  | 2a4* | 2a5 |
| Rewoteric ® AM C (Evonik Goldschmidt GmbH, INCI: Sodium Cocoamphoacetate, 32% strength) | 15% | 15% |
| TEGO ® betaine F 50 (Evonik Goldschmidt GmbH, INCI: Cocamidopropyl Betaine, 38% strength) | 13% | 13% |
| Rewopol ® SB F 12 P (Evonik Goldschmidt GmbH, INCI: Disodium Lauryl Sulfosuccinate 95% strength) | 3.8% | 3.8% |
| Water, demineralized | to 100% | |
| Cap01 |  | 0.5% |

*Comparison example not according to the invention

The test results are summarized in Table 2-4.

TABLE 2-4

Results of the handwashing test

|  | Test formulation | |
|---|---|---|
|  | 2a4* | 2a5 |
| Foaming behavior | 2.2 | 2.9 |
| Foam volume | 1.7 | 2.3 |
| Foam creaminess | 1.9 | 2.7 |
| Skin sensation during washing | 3.3 | 3.6 |
| Skin smoothness directly after application | 2.3 | 2.8 |
| Skin softness directly after application | 2.7 | 2.9 |
| Skin smoothness after 3 min. | 3.2 | 3.5 |
| Skin softness after 3 min. | 3.1 | 3.5 |

*Comparison example not according to the invention

The results of the handwashing test are shown in Table 2-4. By means of the measured results, it is evident that the formulation 2a5 according to the invention using Cap01 brings about a superior skin sensation during and after washing in comparison to the comparison formulation 2a4. In addition, it is evident by means of the measured values that the formulation 2a5 according to the invention containing Cap01 brings about an improvement of the foam properties in the polyether-free surfactant system.

In summary, it can be stated that Cap01 has a markedly positive influence in conventional polyether-containing and polyether-free surfactant formulations both on the foam quality and also on the skin sensation during and after use.

Example 3

Testing of the Solubilizing Properties

The solubilizing properties of Cap01 were tested by clearly dissolving the water-insoluble oil isopropyl myristate (Evonik Goldschmidt GmbH, TEGOSOFT® M) in a surfactant solution consisting of 40% by weight of sodium lauryl ether sulfate (Cognis, Texapon® NSO, 28% strength), 10% by weight of cocamidopropylbetaine (Evonik Goldschmidt GmbH, TEGO® betaine F 50, 38% strength) and 0.5% by weight of solubilizer additive (see examples 3a3, 3a4, 3a6 and 3a7). For comparison, the oil was dissolved in the pure surfactant solution (see examples 3a1 and 3a2 Table 3-1) without solubilizer additive.

The market standard employed was PEG-7 glyceryl cocoate (Evonik Goldschmidt GmbH, TEGOSOFT® GC) (see examples 3a6, 3a7 and 3a8 Table 3-1).

Table 3-1 indicates the amount of isopropyl myristate (Evonik Goldschmidt GmbH, TEGOSOFT® M) which it was additionally possible to clearly dissolve in the respective system. Above this amount, turbidity occurs.

Cap01 has a marked solubilizing action that exceeds the market standard PEG-7 glyceryl cocoate (Evonik Goldschmidt GmbH, TEGOSOFT® GC).

TABLE 3-1

Formulations and results - solubilizing experiments

| | [% by weight] Example | | | | | | | |
|---|---|---|---|---|---|---|---|---|
| | 3a1* | 3a2* | 3a3 | 3a4 | 3a5 | 3a6* | 3a7* | 3a8* |
| Texapon ® NSO (Cognis, INCI: Sodium Laureth Sulfate, 28% strength) | 40 | 40 | 40 | 40 | 40 | 40 | 40 | 40 |
| TEGO ® betaine F 50 (Evonik Goldschmidt GmbH, INCI: Cocamidopropyl Betaine, 38% strength) | 10 | 10 | 10 | 10 | 10 | 10 | 10 | 10 |
| TEGOSOFT ® M (Evonik Goldschmidt GmbH, INCI: Isopropyl Myristate) | 0.5 | 0.6 | 1.0 | 1.5 | 1.6 | 1.0 | 1.1 | 1.2 |
| Cap01 | | | 0.5 | 0.5 | 0.5 | | | |
| TEGOSOFT ® GC (Evonik Goldschmidt GmbH, INCI: PEG-7 Glyceryl Cocoate) | | | | | | 0.5 | 0.5 | 0.5 |
| Water | | | | to 100.0 | | | | |
| Appearance | clear | cloudy | clear | clear | cloudy | clear | clear | cloudy |

*Comparison example not according to the invention

In summary, it can be said that the examples indicated unequivocally demonstrate the thickening, the caring, foam-promoting and the solubilizing action of Cap01, the efficacy of the comparison substances (market standards) in some cases being markedly exceeded.

Example 4

Further Formulation Examples

These examples show exemplary representatives of a multiplicity of formulations according to the invention.

If the preparation of the formulation necessitates beforehand the separate preparation or mixing of formulation constituents, this is designated as a multiphase preparation.

If a two-phase preparation is necessary, the two phases are marked by A and B in the tables indicated.

In the case of three-phase processes, the three phases are named as A, B and C.

Formulation Example 1

Shampoo, PEG- & Sulfate-Free

| | |
|---|---|
| REWOTERIC ® AMC, Evonik Goldschmidt GmbH, 32% strength, (INCI: Sodium Cocoamphoacetate) | 15.00% |
| REWOPOL ® SB F 12 P, Evonik Goldschmidt GmbH, 96% strength, (INCI: Disodium Lauryl Sulfosuccinate) | 3.80% |
| Cap01 | 0.50% |

-continued

| | |
|---|---|
| Perfume | 0.30% |
| Water | 66.10% |
| TEGO ® betaine F 50, Evonik Goldschmidt GmbH, 38% strength, (INCI: Cocamidopropyl Betaine) | 13.00% |
| ANTIL ® HS 60, Evonik Goldschmidt GmbH, (INCI: Cocamidopropyl Betaine; Glyceryl Laurate) | 1.00% |
| Citric Acid, 30% strength | q.s. |
| Preservative | 0.30% |

Formulation Example 2

Mild Hair & Body Wash

| | |
|---|---|
| Plantacare ® 1200 UP, Cognis, 50% strength, (INCI: Lauryl Glucoside) | 11.40% |
| Plantacare ® 818 UP, Cognis, 51% strength, (INCI: Coco Glucoside) | 5.60% |
| Water | 63.00% |
| Cap01 | 0.50% |
| TEGOSOFT ® LSE 65 K SOFT, Evonik Goldschmidt GmbH, (INCI: Sucrose Cocoate) | 1.50% |
| TEGO ® betaine F 50, Evonik Goldschmidt GmbH, 38% strength, (INCI: Cocamidopropyl Betaine) | 18.00% |
| Perfume, preservative | q.s. |
| Citric Acid, 30% | q.s. |

Formulation Example 3

Moisturizing Body Wash

| | | | |
|---|---|---|---|
| A | TEXAPON ® NSO, Cognis, 28% strength, (INCI: Sodium Laureth Sulfate) | | 30.00% |
| | Cap01 | | 0.70% |
| | Perfume | | 0.30% |
| B | Water | | 55.40% |
| | TEGOCEL ® fluid HPM 4000, Evonik Goldschmidt GmbH, (INCI: Hydroxypropyl Methylcellulose) | | 1.20% |
| | TEGO ® betaine C 60, Evonik Goldschmidt GmbH, 46% strength, (INCI: Cocamidopropyl Betaine) | | 8.10% |
| | TEGOSOFT ® APM, Evonik Goldschmidt GmbH, (INCI: PPG-3 Myristyl Ether) | | 1.00% |
| | TEGO ® Pearl N 300, Evonik Goldschmidt GmbH, (INCI: Glycol Distearate; Laureth-4; Cocamidopropyl Betaine) | | 2.00% |
| | REWODERM ® LI S 80, Evonik Goldschmidt GmbH, (INCI: PEG-200 Hydrogenated Glyceryl Palmate; PEG-7 Glyceryl Cocoate) | | 1.00% |
| | Preservative | | 0.60% |
| | Citric Acid, 30% strength | | q.s. |

Formulation Example 4

Clear Shower Gel for Dry Skin

| | |
|---|---|
| Cap01 | 1.00% |
| TAGAT ® CH 40, Evonik Goldschmidt GmbH, (INCI: PEG-40 Hydrogenated Castor Oil) | 2.50% |
| Perfume | 0.30% |
| TEXAPON ® NSO, Cognis, 28% strength, (INCI: Sodium Laureth Sulfate) | 42.90% |
| Water | 39.30% |
| TEGO ® betaine F 50, Evonik Goldschmidt GmbH, 38% strength, (INCI: Cocamidopropyl Betaine) | 10.70% |
| LACTIL ®, Evonik Goldschmidt GmbH, (INCI: Sodium Lactate; Sodium PCA; Glycine; Fructose; Urea; Niacinamide; Inositol; Sodium Benzoate; Lactic Acid) | 1.00% |
| ANTIL ® 171, Evonik Goldschmidt GmbH, (INCI: PEG-18 Glyceryl Oleate/Cocoate) | 2.00% |
| Preservative | 0.30% |

Formulation Example 5

Mild Facial Cleansing Foam

| | | | |
|---|---|---|---|
| A | Water | | 82.20% |
| | TEGO ® Cosmo C 100, Evonik Goldschmidt GmbH, (INCI: Creatine) | | 0.25% |
| | TEGOCEL ® HPM 50, Evonik Goldschmidt GmbH, (INCI: Hydroxypropyl Methylcellulose) | | 0.50% |
| B | TEGO ® betaine 810, Evonik Goldschmidt GmbH, 38% strength, (INCI: Capryl/Capramidopropyl Betaine) | | 6.60% |
| | REWOPOL ® SB CS 50 B, Evonik Goldschmidt GmbH, 40% strength, (INCI: Disodium PEG-5 Laurylcitrate Sulfosuccinate; Sodium Laureth Sulfate) | | 8.00% |
| | Cap01 | | 0.70% |
| | Perfume | | 0.25% |
| | LACTIL ®, Evonik Goldschmidt GmbH, (INCI: Sodium Lactate; Sodium PCA; Glycine; Fructose; Urea; Niacinamide; Inositol; Sodium Benzoate; Lactic Acid) | | 1.00% |
| | Panthenol | | 0.20% |
| | Preservative | | 0.30% |

Formulation Example 6

Clear Moisturizing Shower Gel

| | |
|---|---|
| TEXAPON ® NSO, Cognis, 28% strength, (INCI: Sodium Laureth Sulfate) | 37.00% |
| Cap01 | 1.00% |
| Perfume | 0.30% |
| Water | 42.00% |
| REWOTERIC ® AMC, Evonik Goldschmidt GmbH, 32% strength, (INCI: Sodium Cocoamphoacetate) | 9.00% |
| TEGO ® betaine 810, Evonik Goldschmidt GmbH, 38% strength, (INCI: Capryl/Capramidopropyl Betaine) | 7.60% |
| LACTIL ®, Evonik Goldschmidt GmbH, (INCI: Sodium Lactate; Sodium PCA; Glycine; Fructose; Urea; Niacinamide; Inositol; Sodium Benzoate; Lactic Acid) | 1.00% |
| Citric Acid, 30% strength | 1.30% |
| REWODERM ® LI S 80, Evonik Goldschmidt GmbH, (INCI: PEG-200 Hydrogenated Glyceryl Palmate; PEG-7 Glyceryl Cocoate) | 0.50% |
| Preservative | 0.30% |

Formulation Example 7

Shampoo, Peg- & Sulfate-Free

| | |
|---|---|
| REWOTERIC ® AM C, Evonik Goldschmidt GmbH, 32% strength, (INCI: Sodium Cocoamphoacetate) | 15.00% |
| Plantapon ACG 50, Cognis (INCI: Disodium Cocoyl Glutamate) | 3.80% |
| Cap01 | 1.00% |
| Perfume | 0.30% |
| Water | 66.30% |
| TEGO ® betaine F 50, Evonik Goldschmidt GmbH, 38% strength, (INCI: Cocamidopropyl Betaine) | 10.00% |
| VARISOFT ® PATC, Evonik Goldschmidt GmbH, (INCI: Palmitamidopropyltrimonium Chloride) | 2.30% |
| REWOMID ® SPA, Evonik Goldschmidt GmbH, (INCI: Isostearamide MIPA) | 1.00% |
| Preservative | 0.30% |
| Citric Acid, 30% strength | q.s. |

Formulation Example 8

Shower for Sensitive Skin

| | |
|---|---|
| TEXAPON ® NSO, Cognis, 28% strength (INCI: Sodium Laureth Sulfate) | 15.00% |
| Cap01 | 0.50% |
| Perfume | 0.30% |
| PGFAC-S, Cognis (INCI: Sodium cocoyl hydrolyzed wheat protein glutamate) | 1.50% |
| REWOPOL SB CS 50 B, Evonik Goldschmidt GmbH, 40% strength, (INCI: Disodium PEG-5 Laurylcitrate Sulfosuccinate; Sodium Laureth Sulfate) | 7.50% |
| Water | 60.10% |
| TEGO ® betaine F 50, Evonik Goldschmidt GmbH, 38% strength, (INCI: Cocamidopropyl Betaine) | 9.00% |
| TEGO ® betaine 810, Evonik Goldschmidt GmbH, 38% strength, (INCI: Capryl/Capramidopropyl Betaine) | 4.00% |
| ANTIL ® 200, Evonik Goldschmidt GmbH, (INCI: PEG-200 Hydrogenated Glyceryl Palmate; PEG-7 Glyceryl Cocoate) | 1.80% |
| Preservative | 0.30% |

Formulation Example 9

Shampoo, Peg- & Sulfate-Free

| | | |
|---|---|---|
| A | REWOTERIC ® AMC, Evonik Goldschmidt GmbH, 32% strength, (INCI: Sodium Cocoamphoacetate) | 20.00% |
| | REWOPOL ® SB F 12 P, Evonik Goldschmidt, 96% strength, (INCI: Disodium Lauryl Sulfosuccinate) | 5.90% |
| | Cap01 | 0.70% |
| B | Water | 66.20% |
| | Citric Acid, 30% strength | 3.60% |
| C | ANTIL ® HS 60, Evonik Goldschmidt GmbH, (INCI: Cocamidopropyl Betaine; Glyceryl Laurate) | 3.00% |
| | Preservative | 0.60% |

Formulation Example 10

Mild Body Wash

| | | |
|---|---|---|
| A | TEXAPON ® NSO Cognis 28% strength, (INCI: Sodium Laureth Sulfate) | 30.00% |
| | Cap01 | 0.50% |
| | ABIL ® B 8832, Evonik Goldschmidt GmbH, (INCI: Bis-PEG/PPG-20/20 Dimethicone) | 0.30% |
| | Perfume | 0.30% |
| B | Water | 53.00% |
| | TEGOCEL ® fluid HPM 4000, Evonik Goldschmidt GmbH, (INCI: Hydroxypropyl Methylcellulose) | 1.20% |
| | Citric Acid Monohydrate | 0.50% |
| | REWOTERIC ® AM C, Evonik Goldschmidt GmbH, 32% strength, (INCI: Sodium Cocoamphoacetate) | 10.00% |
| | TEGO ® Pearl N 300, Evonik Goldschmidt GmbH, (INCI: Glycol Distearate; Laureth-4; Cocamidopropyl Betaine) | 2.00% |
| | REWODERM ® LI S 80, Evonik Goldschmidt GmbH, (INCI: PEG-200 Hydrogenated Glyceryl Palmate; PEG-7 Glyceryl Cocoate) | 1.60% |
| | Preservative | 0.60% |
| | Citric Acid, 30% strength | q.s. |

Formulation Example 11

Sprayable Hairmilk, Peg-Free

| | | |
|---|---|---|
| A | Water | 95.30% |
| | Lactic Acid, 80% strength | 0.40 |
| B | TEGO ® AMIDE S 18, Evonik Goldschmidt GmbH, (INCI: Stearamidopropyl Dimethylamine) | 1.20% |
| | TEGIN ® G 1100 Pellets, Evonik Goldschmidt GmbH, (INCI: Glycol Distearate) | 0.60% |
| | TEGO ® Care PS, Evonik Goldschmidt GmbH, (INCI: Methyl Glucose Sesquistearate) | 1.20% |
| | TEGOSOFT ® DEC, Evonik Goldschmidt GmbH, (INCI: Diethylhexyl Carbonate) | 0.30% |
| | Cap01 | 1.00% |
| | Perfume, preservative | q.s. |

Formulation Example 12

Body Cleansing Foam

| | |
|---|---|
| TEXAPON ® NSO, Cognis, 28% strength (INCI: Sodium, Laureth Sulfate) | 14% |
| Perfume | 0.3% |
| Cap01 | 0.5% |
| REWOTERIC ® AM C, Evonik Goldschmidt GmbH, 32% strength (INCI: Sodium Cocoamphoacetate) | 8% |
| Water | 75.2% |
| TEGOCEL ® HPM 50, Evonik Goldschmidt GmbH (INCI: Hydroxypropyl Methylcellulose) | 0.5% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 1% |
| Citric Acid Monohydrate | 0.5% |

Formulation Example 13

Formulation Example Clear Conditioning Shampoo

| | |
|---|---|
| TEXAPON ® NSO, Cognis, 28% strength (INCI: Sodium Laureth Sulfate) | 32.00% |
| VARISOFT ® PATC, Evonik Goldschmidt GmbH(INCI: Palmitamidopropyltrimonium Chloride) | 1.50% |
| REWODERM ® LI S 80, Evonik Goldschmidt GmbH (INCI: PEG-200 Hydrogenated Glyceryl Palmate; PEG-7 Glyceryl Cocoate) | 2.00% |
| Cap01 | 0.50% |
| Perfume | 0.25% |
| Water | 54.05 |
| TEGO ® Cosmo C 100, Evonik Goldschmidt GmbH, (INCI: Creatine) | 1.00% |
| Jaguar C-162, Rhodia (INCI: Hydroxypropyl Guar Hydroxypropyltrimonium Chloride) | 0.20 |
| TEGO ® betaine F 50, Evonik Goldschmidt GmbH, 38% strength (INCI: Cocamidopropyl Betaine) | 8.00% |
| NaCl | 0.50% |
| Preservative | q.s. |

Formulation Example 14

Formulation Example Pearlized Shampoo

| | |
|---|---|
| TEXAPON ® NSO, Cognis, 28% strength (INCI: Sodium Laureth Sulfate) | 32.00% |
| Cap01 | 0.50% |
| Perfume | 0.25% |
| Water | 55.25 |
| TEGO ® betaine F 50, Evonik Goldschmidt GmbH, 38% strength (INCI: Cocamidopropyl Betaine) | 8.00% |
| TEGO ® Pearl N 300 Evonik Goldschmidt GmbH (INCI: Glycol Distearate; Laureth-4; Cocamidopropyl Betaine) | 2.00% |
| ANTIL ® 171 Evonik Goldschmidt GmbH (INCI: PEG-18 Glyceryl Oleate/Cocoate) | 1.50% |
| NaCl | 0.50% |
| Preservative | q.s. |

Formulation Example 15

Formulation Example Rinse-Off Conditioner

| | |
|---|---|
| Water | 90.20% |
| VARISOFT ® EQ 65, Evonik Goldschmidt GmbH (INCI: Distearyl Dimonium Chloride, Cetearyl Alcohol) | 2.00% |
| VARISOFT ® BT 85, Evonik Goldschmidt GmbH (INCI: Behentrimonium Chloride) | 2.00% |
| Cap01 | 0.80% |
| TEGO ® Alkanol 1618, Evonik Goldschmidt GmbH (INCI: Cetearyl Alcohol) | 5.00 |
| Preservative, Perfume | q.s. |

Formulation Example 16

Formulation Example Clear Conditioning Shampoo

| | |
|---|---|
| TEXAPON ® NSO, Cognis, 28% strength (INCI: Sodium Laureth Sulfate) | 32.00% |
| ANTIL ® 200, Evonik Goldschmidt GmbH (INCI: PEG-200 Hydrogenated Glyceryl Palmate; PEG-7 Glyceryl Cocoate) | 2.00% |
| Cap01 | 1.00% |
| Perfume | 0.25% |
| Water | 56.25 |
| Polymer JR 400, Amerchol (INCI: Polyquaternium-10) | 0.20 |
| TEGO ® betaine F 50, Evonik Goldschmidt GmbH, 38% strength (INCI: Cocamidopropyl Betaine) | 8.00% |
| NaCl | 0.30% |
| Preservative | q.s. |

The invention claimed is:

1. A formulation for the cleansing and care of human or animal body parts containing sorbitan carboxylic acid esters, wherein the carboxylic acid component of the sorbitan carboxylic acid ester is derived from a carboxylic acid containing 6 to 10 carbon atoms and the sorbitan carboxylic acid esters have a hydroxyl number (OH number) of greater than 350, wherein said formulation is essentially free of polyethers and polyether-containing compounds, and wherein 1.2 to 2 mol of carboxylic acid per one mole of sorbitol from which the sorbitan carboxylic acid ester is derived is esterified.

2. The formulation as claimed in claim 1, wherein said formulation contains from 0.01% by weight to 10% by weight of sorbitan carboxylic acid ester based on the total formulation.

3. The formulation as claimed in claim 1, wherein the formulation is an aqueous surfactant formulation.

4. The formulation as claimed in claim 1, wherein the formulation is free of polyethers and polyether-containing compounds.

5. The formulation as claimed in claim 1, wherein the sorbitan carboxylic acid esters contained have an acid number of less than 20.

6. The formulation as claimed in claim 1, wherein the sorbitan carboxylic acid esters contained have an iodine number of less than 30.

7. The formulation as claimed in claim 1, wherein the sorbitan carboxylic acid esters contained have a viscosity of 100 to 20 000 mPa·s.

8. A process for preparing the formulation as claimed in claim 1, comprising
   A) dehydrating sorbitol, and
   B) reacting the dehydrated sorbitol with at least one compound selected from the group consisting of carboxylic acids containing 6 to 10 carbon atoms, carboxylic acid esters and carboxylic acid ester mixtures, in which the carboxylic acid component contains 6 to 10 carbon atoms, wherein said formulation is essentially free of polyethers and polyether-containing compounds, and wherein 1.2 to 2 mol of carboxylic acid per one mole of sorbitol from which the sorbitan carboxylic acid ester is derived is esterified.

9. The formulation of claim 1, wherein said sorbitan carboxylic acid ester is a viscosity regulator, care active ingredient, foam booster or solubilizer.

10. The process of claim 8 further comprising C) isolating the formed sorbitan esters from step B).

* * * * *